(12) United States Patent
Tochimura et al.

(10) Patent No.: US 8,105,354 B2
(45) Date of Patent: Jan. 31, 2012

(54) TRIANGULAR SUTURE NEEDLE

(75) Inventors: Yoshimasa Tochimura, Tochigi (JP); Kanji Matsutani, Tochigi (JP); Masaki Mashiko, Tochigi (JP)

(73) Assignee: MANI, Inc., Utsunomiya-shi, Tochigi (JP)

( * ) Notice: Subject to any disclaimer, the term of this patent is extended or adjusted under 35 U.S.C. 154(b) by 243 days.

(21) Appl. No.: 12/373,178

(22) PCT Filed: Jul. 10, 2007

(86) PCT No.: PCT/JP2007/063705
§ 371 (c)(1),
(2), (4) Date: Mar. 12, 2009

(87) PCT Pub. No.: WO2008/007655
PCT Pub. Date: Jan. 17, 2008

(65) Prior Publication Data
US 2009/0292312 A1 Nov. 26, 2009

(30) Foreign Application Priority Data
Jul. 12, 2006 (JP) .................................. 2006-191591

(51) Int. Cl.
*A61B 17/06* (2006.01)
(52) U.S. Cl. ...................................................... 606/223
(58) Field of Classification Search .................. 606/139, 606/144–150, 222–227; 112/222–227; D24/145–146
See application file for complete search history.

(56) References Cited

U.S. PATENT DOCUMENTS
5,100,432 A 3/1992 Matsutani
5,263,974 A * 11/1993 Matsutani et al. ............ 606/223

FOREIGN PATENT DOCUMENTS
JP 3-244445 A 10/1991
JP 2005-532874 A 11/2005
WO 2004/006987 A 1/2004

\* cited by examiner

*Primary Examiner* — Melanie Tyson
*Assistant Examiner* — Son Dang

(57) ABSTRACT

A triangular suture needle having a low thrust resistance and a press mold suitable for manufacturing the same are provided. The triangular suture needle includes: an angular triangular prism-shaped part (100a) on the needlepoint side; a rounded triangular prism-shaped part (100b) connecting to the needle base side of said triangular prism-shaped part; and a thread attaching part (100c) in a needle base end. The entire angular triangular prism-shaped part (100a) is ground, forming a pointed, sharpened part (100d) with a sharp tip. Furthermore, width (w1) of the thickest portion of the sharpened part (100d) is greater than width (w2) of the rounded triangular prism-shaped part connecting to that portion.

1 Claim, 9 Drawing Sheets

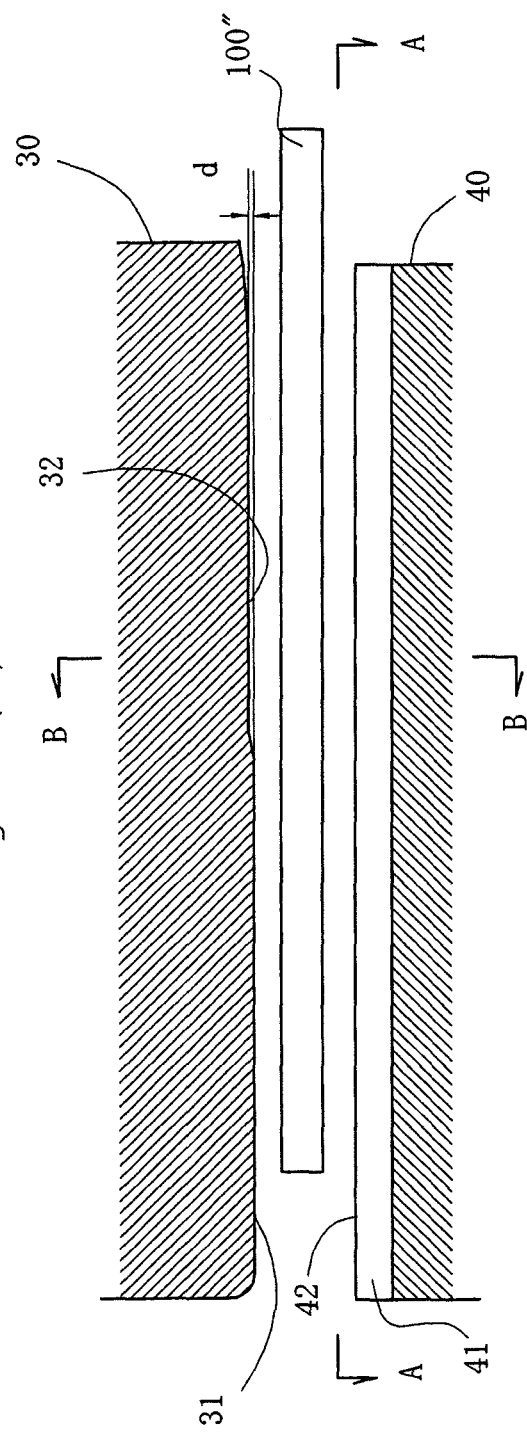
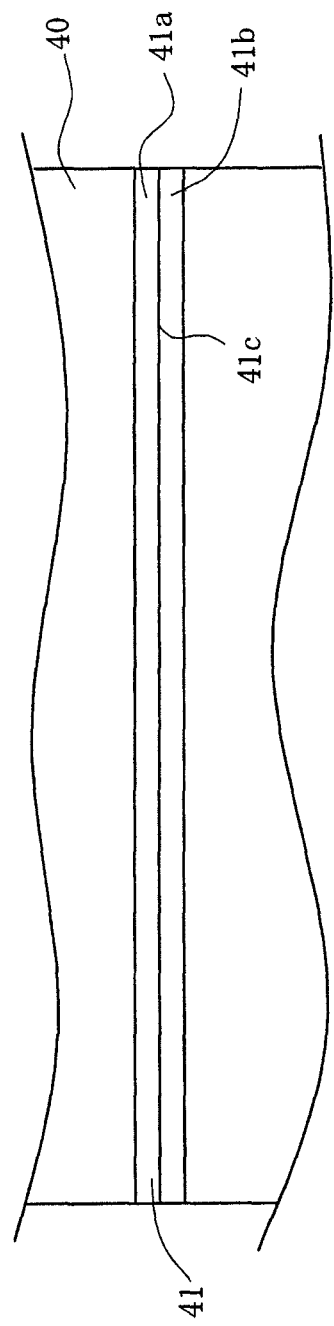

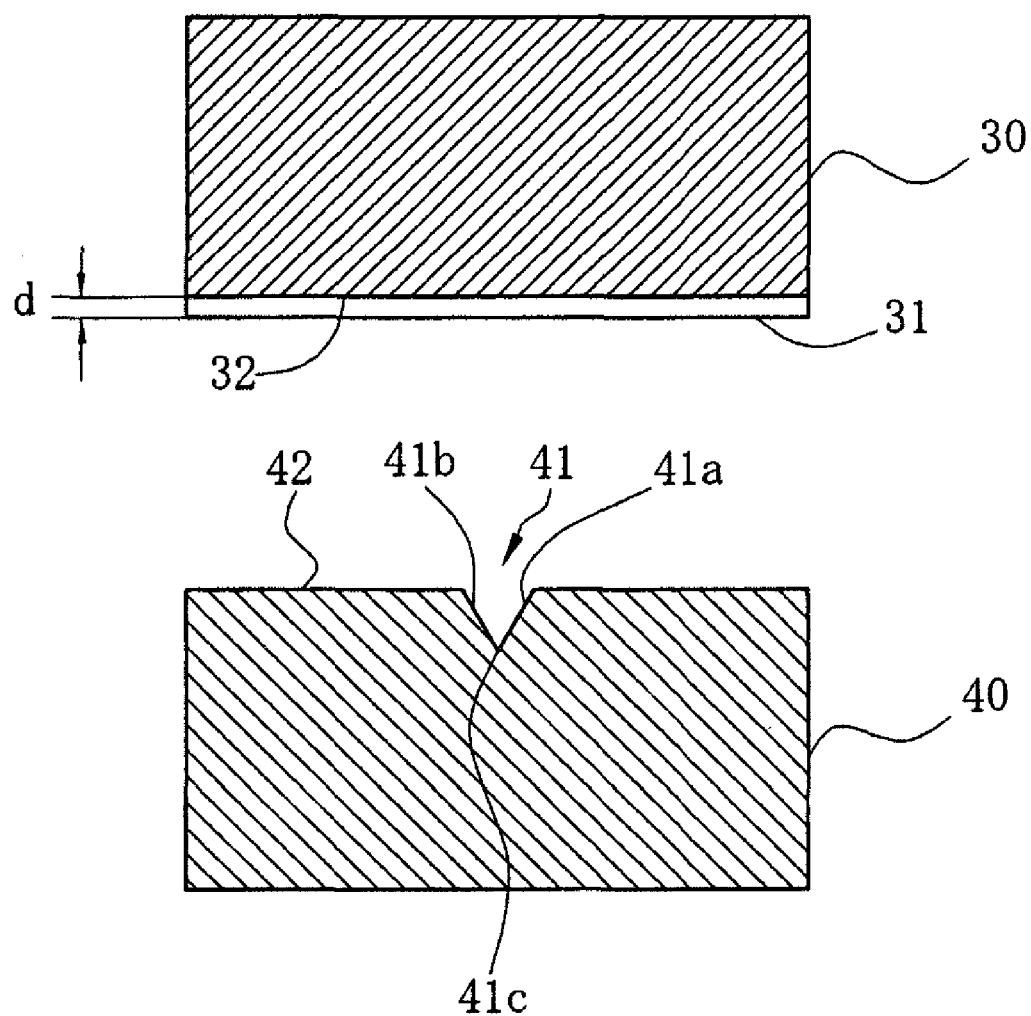

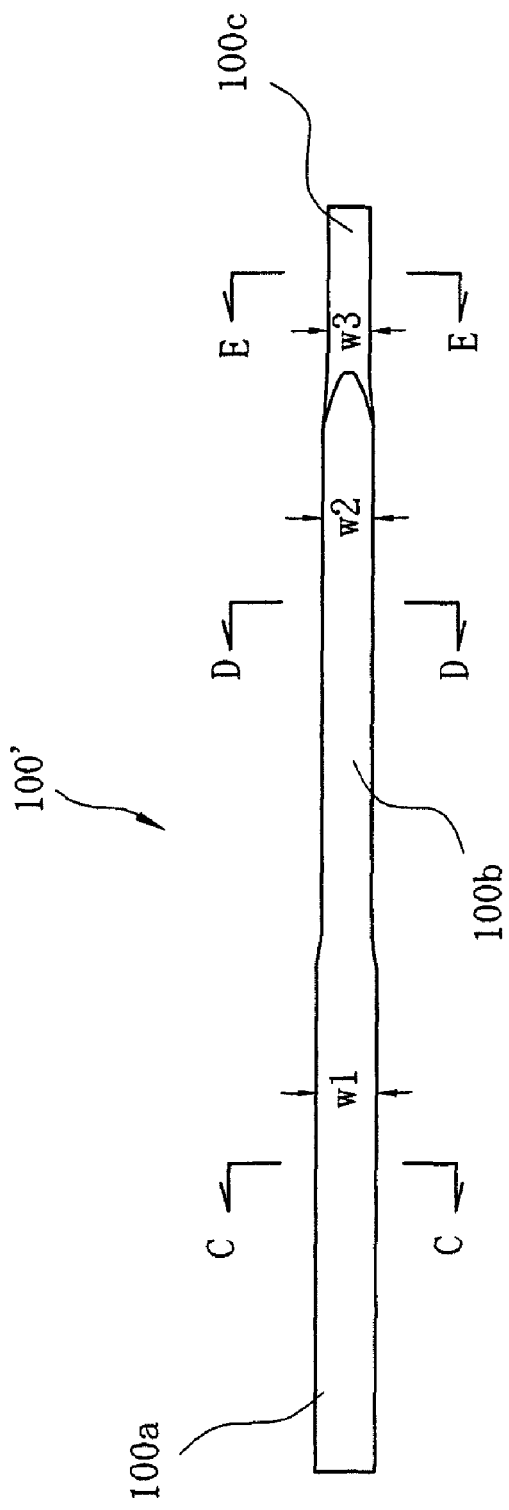

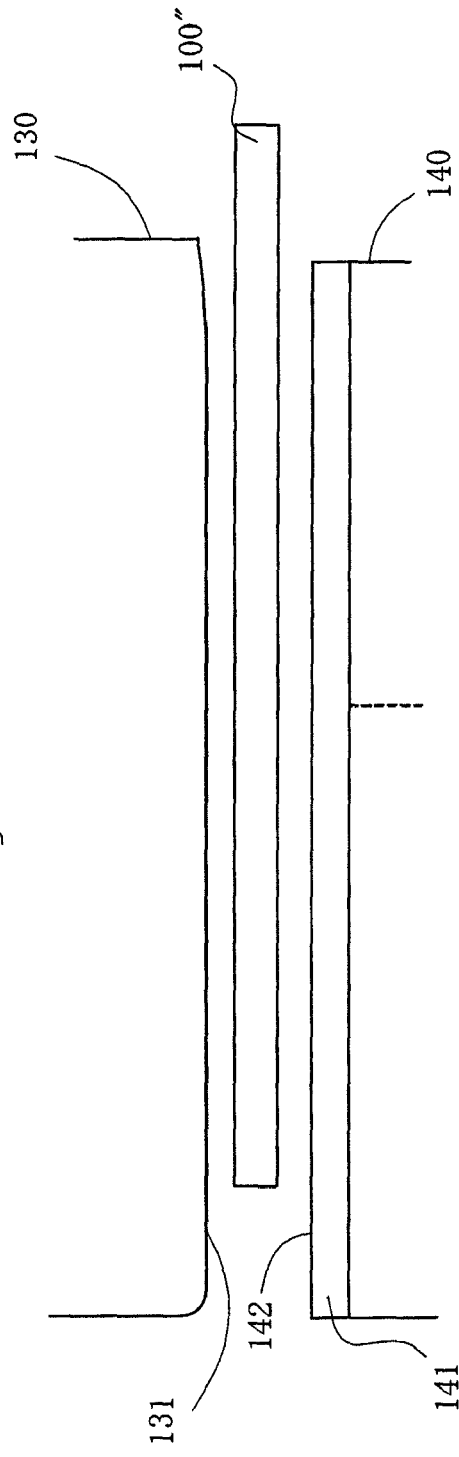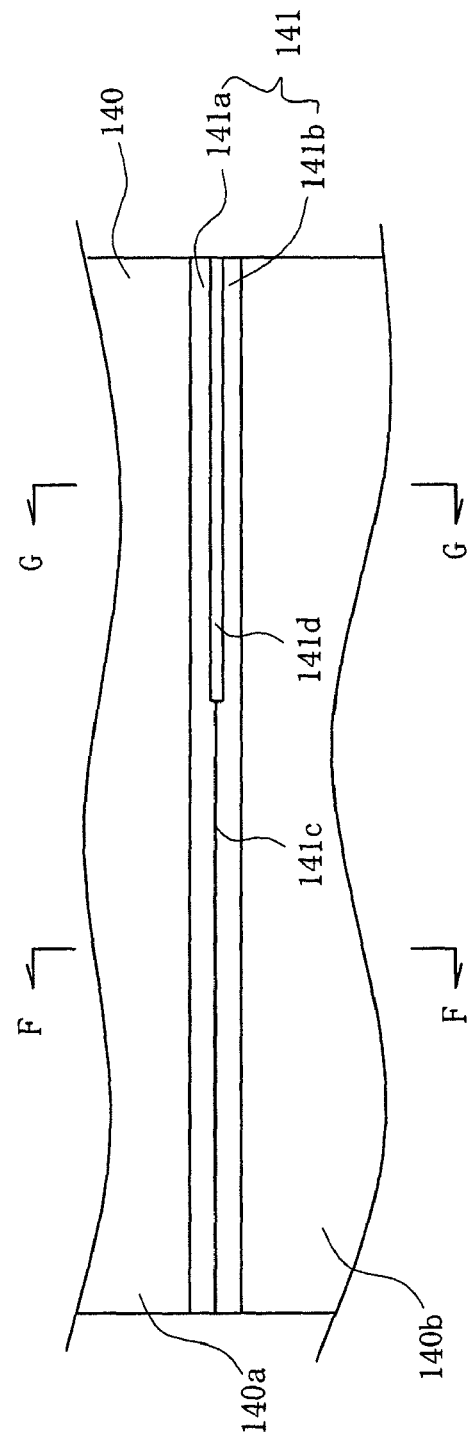

Fig. 8

EVALUATION OF CUTTING ABILITY BY DOCTORS

|  | FIRST EMBODIMENT (φ0.5) | SECOND EMBODIMENT (φ0.5) | CONVENTIONAL EXAMPLE (φ0.5) |
|---|---|---|---|
| DOCTOR 1 | A | A | B |
| DOCTOR 2 | A | A | B |
| DOCTOR 3 | A | A | A |
| DOCTOR 4 | A | A | B |
| DOCTOR 5 | A | B | B |
| DOCTOR 6 | B | A | C |
| DOCTOR 7 | A | A | B |
| DOCTOR 8 | A | A | B |
| DOCTOR 9 | A | A | B |
| DOCTOR 10 | A | A | B |

A : GOOD    B : AVERAGE    C : POOR

TRIANGULAR SUTURE NEEDLE

TECHNICAL FIELD

The present invention relates to a suture needle for medical use and particularly relates to a triangular suture needle having a blade with a triangular cross section, and a press mold suitable for manufacturing the triangular suture needle.

BACKGROUND ART

Suture needles for medical use are manufactured through processes, such as pressing a stainless steel wire rod having a predetermined diameter, which is formed typically through a drawing process, into a predetermined external shape, cutting it into a predetermined length, grinding each of them to form a sharpened part, forming a thread attaching part, bending the entirety into a half arc shape, and subjecting it to a finishing treatment.

The suture needle for medical use may be a polygonal needle with a polygonal cross section mainly used for suturing skin, or a round needle with a round cross section mainly used for suturing blood vessels and internal organs.

The polygonal needle, a triangular suture needle having a triangular cross section, for example, is formed as follows. First, a round-bar material is formed into a triangular prism shape using a press mold while leaving the needle base as is. The press mold used for this formation is divided into an upper mold and a lower mold, where the lower mold forms a V-shaped groove and two sides of a triangular prism, and the upper mold forms the remaining side of the triangular prism-shaped part with a flat surface. The pressed material has the thread attaching part on the needle base side left as a round bar and the other end made into a triangular prism-shaped part. With the triangular suture needle, three sides of the triangular prism-shaped part are ground to sharpen the tip so as to facilitate insertion of the suture needle into a living tissue and reduce thrust resistance when inserting.

FIG. 9 is an oblique perspective of an exemplary conventional triangular suture needle. A triangular suture needle 10 shown in this diagram has a hole 12 formed in one base end 11a of a thread attaching part 11 using such as a laser. A suture thread 20 is inserted in the hole 12 and calked and fixed.

The part from the thread attaching part 11 of the triangular suture needle 10 to the tip, which is formed into a triangular prism by pressing, is ground to form a sharp needlepoint 14, and three cutting blades 15 continuous from the needlepoint 14 are formed corresponding to the respective corners of the triangle.

With the conventional triangular suture needle 10, the diameter of a sharpened part forming the cutting blades 15 of the triangular prism-shaped part increases it's diameter gradually, and the rest is a triangular prism-shaped part of a constant diameter (parallel part).

Since, with the conventional triangular suture needle, since a round bar is press formed into a triangular prism and the tip is ground to form cutting blades, areas of the circle and the triangle of the triangular prism-shaped part on the needle base side are approximately the same. Therefore, diameter of the fattest portion of the triangular prism-shaped part, namely width of each side of the triangle configuring the cross section of the triangular prism is slightly greater than that of the circular part of the needle base, and is configured as a rounded triangular prism-shaped part. Furthermore, diameter of the cutting blade portion (sharpened part) increasing in diameter is less than that of the triangular prism-shaped part of the parallel part. In other words, the width of the aforementioned respective sides decreases.

DISCLOSURE OF INVENTION

Problem to be Solved by the Invention

In the case of suturing a wound, thrust resistance continues to rise gradually as the sharpened part thrusts a tissue. Thrust resistance reaches to it's peak where an intermediate position of the sharpened part thrusts a tissue, in other words, where the diameter increasing rate (tapering angle) exceeds a predetermined threshold thrusts a tissue, and after the point or the peak, the thrust resistance then falls gradually. With the conventional suture needle, the tip angle (tapering angle at the tip) of the sharpened part is relatively large, and there are cases where three cutting blades are not formed at the intermediate position due to variance, thereby increasing the thrust resistance.

If the tip angle of the sharpened part is decreased, the thrust resistance when inserting the tip of the suture needle into the living tissue decreases, but the sharpened part must be elongated in order for that to happen. However, it is difficult to properly grind three surfaces since the grinding operation is performed manually. Sometimes it could happen that only one surface of the needle base side of the sharpened part is ground heavy and the other surfaces are ground weak, sharp cutting blades are formed only on the tip and not on the needle base. Making the sharpened part longer particularly increases that tendency. Therefore, the conventional suture needle has been formed with a short sharpened part and a relatively large tip angle.

The present invention is devised through consideration of the aforementioned problems. An objective thereof is to provide a triangular suture needle reduced of thrust resistance through simple processing.

Means of Solving the Problem

In order to attain the objective described above, a triangular suture needle of the present invention includes: an angular triangular prism-shaped part on the needlepoint side; a rounded triangular prism-shaped part connecting to a needle base side of said triangular prism-shaped part; and a thread attaching part in a needle base end, wherein the angular triangular prism-shaped part is ground, forming a pointed, sharpened part with a sharp tip. The sharpened part may be formed along the entire angular triangular prism-shaped part on the needlepoint. Width of the thickest portion of the sharpened part may be greater than width of the rounded triangular prism-shaped part. Furthermore, tips of blade surfaces configuring cutting blades of the sharpened part may be ground and removed.

EFFECTS OF INVENTION

When thrusting the triangular suture needle of the present invention into a living tissue, it enters the living tissue from the sharp tip of the pointed sharpened part, and progresses while cutting open the living tissue when the rest of the sharpened part is inserted. The diameter increasing rate (tapering angle) of the sharpened part changes as it moves from the tip of the needle to the base. Namely, the diameter increasing rate is higher (large tapering angle) at the tip, it decreases as it approaches the base, and is zero at the parallel part. Until a region of the sharpened part having a certain diameter increasing rate (tapering angle) or greater is passed, thrust resistance continues to increase, and begins to decrease before the entire sharpened part is inserted. Once the pointed sharpened part is completely inserted, the rounded triangular prism-shaped part then enters the living tissue. By making the entire angular triangular prism-shaped part on the needle-point be the sharpened part, cutting blades may be formed up to the parallel part. Therefore, since the region with a peak thrust resistance has cutting blades consistently, the suture needle is user friendly with little thrust resistance. Furthermore, since only the angular portion needs to be ground, it is easy for a worker to recognize the part to grind, and variance is difficult to occur since the cutting blades of the needle base of the sharpened part are completed through weak grinding. Properly grinding three surfaces allows formation of a long sharpened part and reduction in thrust resistance.

Furthermore, in the case of suturing a tough and thick living tissue, it can be speculated that a greater width of the thickest portion of the sharpened part formed along the angular triangular prism-shaped part than that of the rounded triangular prism-shaped part is effective. Since the rounded triangular prism-shaped part has a smaller diameter than the thickest portion of the angular triangular prism-shaped part, this part may pass through the hole formed by the sharpened part without needing to further widen it, and thus there is little thrust resistance. By dividing the triangular prism-shaped part into a angular triangular prism-shaped part and a rounded triangular prism-shaped part to form cutting blades on the triangular prism-shaped part, a sharpened part with a small tip angle may be formed without any variance, and excellent effects of reduced thrust resistance and decreased burden on patients are achieved.

BRIEF DESCRIPTION OF DRAWINGS

FIG. 1 is a diagram showing a press mold according to a first embodiment of the present invention, where FIG. 1(a) is a vertical cross section, and FIG. 1(b) is a diagram showing substantial parts of a lower mold viewed from the line A-A;

FIG. 2 is a cross section cut along the line B-B of FIG. 1;

FIG. 3 is a diagram of a round-bar material after being pressed by an upper mold and the lower mold of FIGS. 1 and 2, where FIG. 3(a) is a top view, FIG. 3(b) is a cross section cut along the line C-C, FIG. 3(c) is a cross section cut along the line D-D, and FIG. 3(d) is a cross section cut along the line E-E;

FIG. 4 is a diagram showing three surfaces of a triangular prism-shaped part on the needlepoint side, where

FIG. 6 is a diagram showing a press mold according to a second embodiment of the present invention, where FIG. 6(a) is a front view, and FIG. 6(b) is a top view of a lower mold;

FIG. 8 is a chart showing results of a blind test for doctors to evaluate cutting ability of a conventional triangular suture needle and the triangular suture needle of the present invention.

Figure 4A:
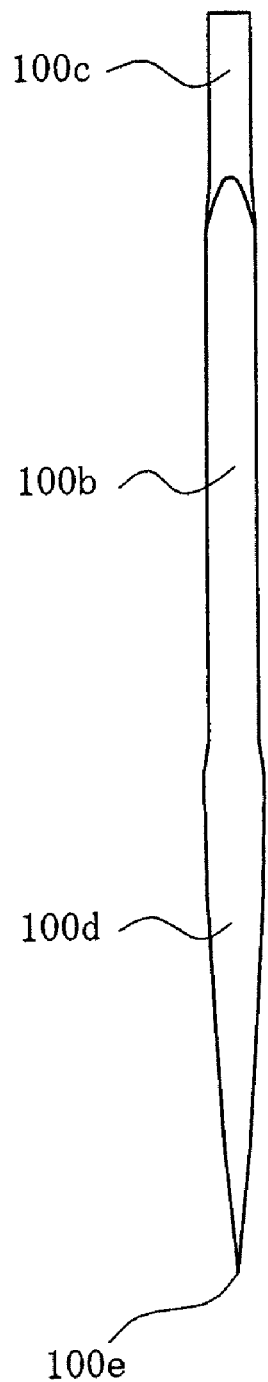
FIG. 4(a) is a top view and FIG. 4(b) is a side view.

DESCRIPTION OF REFERENCE NUMBER 30,130: upper mold
31: first side
32: second side
40,140: lower mold
41,141: V-shaped groove
100: triangular suture needle
100": round-bar material
100a: angular triangular prism-shaped part on the tip side
100b: rounded triangular prism-shaped part on the needle base side
d: step
w1: width of triangular prism-shaped part on the tip side
w2: width of triangular prism-shaped part on the needle base side

BEST MODE OF CARRYING OUT THE INVENTION

Embodiments according to the present invention are described with reference to accompanying drawings forthwith.

FIG. 1 is a diagram showing a press mold according to a first embodiment of the present invention, where FIG. 1(a) is a vertical cross section, and FIG. 1(b) is a diagram showing substantial parts of a lower mold viewed from the line A-A; FIG. 2 is a cross section cut along the line B-B of FIG. 1.

An upper mold 30 is nearly a rectangular parallelepiped in its entirety although it curves towards both left and right ends of FIG. 1. A surface facing a lower mold 40 is divided into a first surface 31 on the needlepoint side and a second surface 32 on the needle base side. Step d is formed between the first surface 31 and the second surface 32 such that the second surface 32 on the needle base side recedes from the first surface 31 of the needlepoint, being further away from the lower mold 40.

A V-shaped groove 41 for forming a triangular prism-shaped part in a round-bar material 100" is formed in the lower mold 40. Furthermore, top surface 42 corresponding to the first surface 31 of the upper mold 30 is formed on top surface of the lower mold 40.

Note that dividing the top surface 42 into a first top surface and a second top surface and forming the same step d therebetween as with that formed on the upper mold 30 may also be considered. While the triangular suture needle of the present invention can be manufactured using this method, since manufacturing cost for the molds is high, it is more advantageous to make the top surface of the lower mold 40 into a flat surface. The step d is preferably 2 to 9% of the diameter of the round-bar material 100". Reasons for the 2% lower limit are that the portion corresponding to the second surface 32 does not become a rounded triangular prism-shaped part, and there is no significant difference in shape of the triangular prism-shaped parts corresponding to the first surface 31 and the second surface 32, and when the portion corresponding to the first surface 31 is ground to form a cutting blade in a subsequent step, the maximum width of the sharpened part does not get larger than the width of the rounded triangular prism-shaped part corresponding to the second surface 32 but is equal thereto. The reason for the 9% upper limit is that exhibition of desired performance with respect to graspability and bending strength is impossible since corners of the triangular prism-shaped part become rounded and closer to a round bar.

Meanwhile, the V-shaped groove 41 has surfaces 41a and 41b forming two surfaces of the triangular prism-shaped part, with a ridge line 41c formed therebetween as a boundary; however, there is no step corresponding to the boundary of the first top surface 31 and the second top surface 32 on respective surfaces 41a and 41b, thus providing a single flat surface. Furthermore, the ridge line 41c is a straight line.

A triangle formed by the two surfaces 41a and 41b of the V-shaped groove 41 and the first surface 31 of the upper mold is an equilateral triangle and has approximately the same area as the cross-sectional area of the round-bar material 100". Meanwhile, a triangle formed by the two surfaces 41a and 41b of the V-shaped groove 41 and the second surface 32 of the upper mold is also an equilateral triangle, but the area thereof is slightly larger than the cross-sectional area of the round-bar material 100".

The round-bar material 100" which becomes a triangular suture needle 100 is fed between the upper mold 30 and the lower mold 40 and then pressed.

FIG. 3 is a diagram of a round-bar material 100' after being pressed by an upper mold 30 and the lower mold 40 of FIGS. 1 and 2, where FIG. 3(a) is a top view, FIG. 3(b) is a cross section cut along the line C-C, FIG. 3(c) is a cross section cut along the line D-D, and FIG. 3(d) is a cross section cut along the line E-E of FIG. 3(a). The pressed round-bar material 100' is made up of a triangular prism-shaped part 100a on the needlepoint side, a triangular prism-shaped part 100b on the needle base side, and a thread attaching part 100c with a round cross section not pressed at all. Combined length of the triangular prism-shaped part 100a on the needlepoint side and the triangular prism-shaped part 100b on the needle base side is the same as the length of the triangular prism-shaped part of the conventional triangular suture needle, and lengths of the triangular prism-shaped part 10a on the needlepoint side and the triangular prism-shaped part 100b on the needle base side are nearly the same.

Since the triangular prism-shaped part 100a on the needlepoint side is an equilateral triangle formed by the two surfaces 41a and 41b of the V-shaped groove 41 and the first surface 31 of the upper mold and has approximately the same area as the cross-sectional area of the round-bar material 100", it becomes an angular triangular prism-shaped part 100a with material penetrating into the corners of the triangle. It is preferable that the triangular prism-shaped part 100a on the needlepoint side slightly protrudes and makes burrs since the corners become sharp. Since the triangular prism-shaped part 100b on the needle base side is rounded because an equilateral triangle formed by the two surfaces 41a and 41b of the V-shaped groove 41 and the second surface 32 of the upper mold and the area is greater than the cross-sectional area of the round-bar material 100", making it difficult for material to penetrate into the corners of the triangle.

Comparison of width w1 of the triangular prism-shaped part 100a, width w2 of the triangular prism-shaped part 100b, and diameter w3 of the thread attaching part 100c shows a relationship of w1>w2>w3.

Figure 4B:
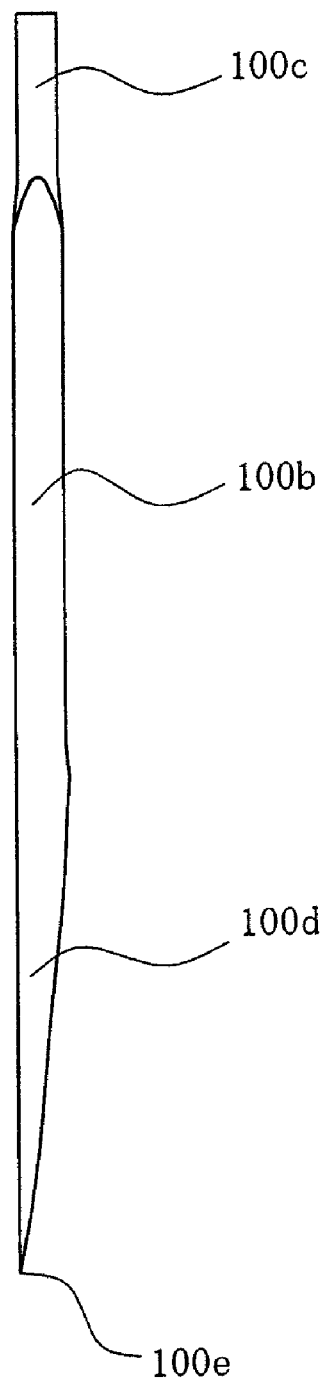
Figure 5:
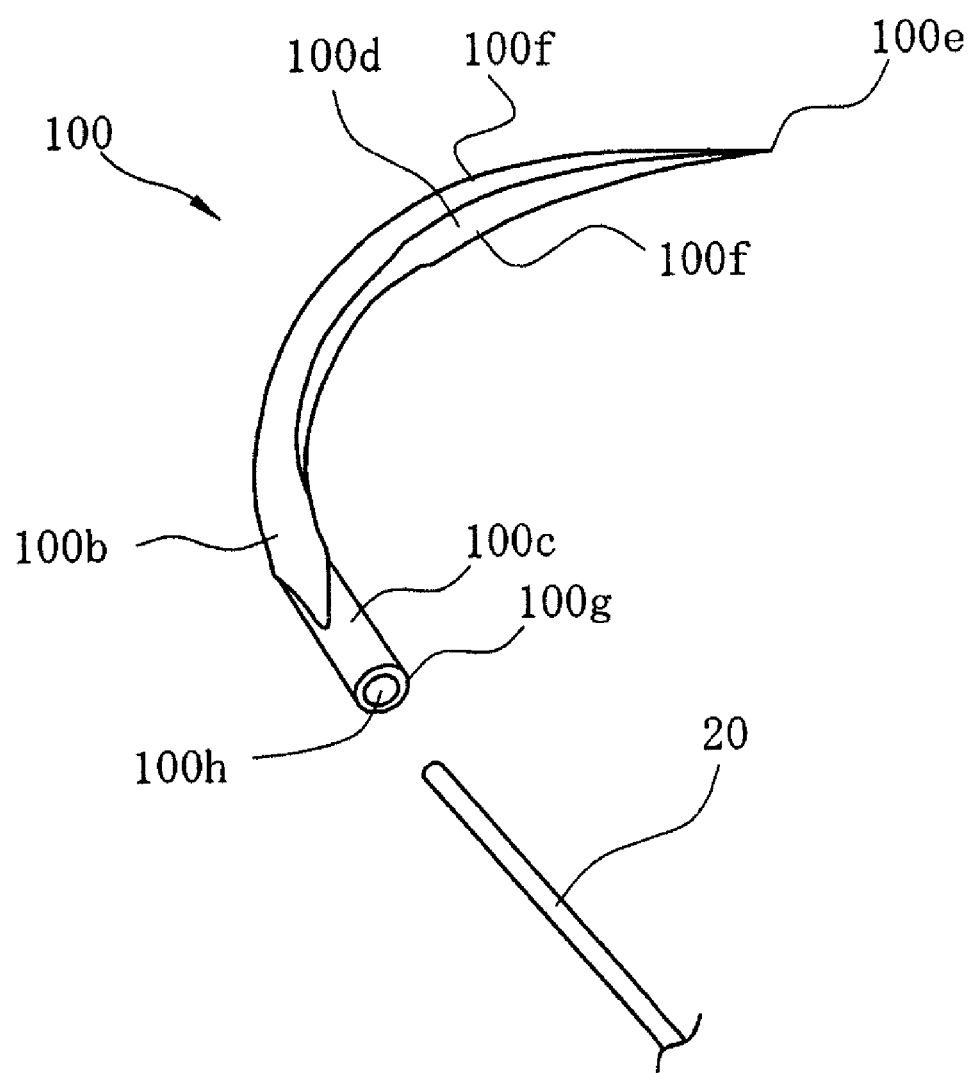
FIG. 5 is an oblique perspective of a triangular suture needle of the present invention.

Afterwards, the three surfaces of the triangular prism-shaped part 100a on the needlepoint side is ground using a grindstone so that the tip is sharpened into a pointed sharpened part 100d, and a needlepoint 100e is sharpened to a point as shown in FIGS. 4(a) and 4(b). The sharpened part 100d is formed along the entire length of the triangular prism-shaped part 100a on the needlepoint side. Afterwards, it is bent to be a triangular suture needle 100 as shown in FIG. 5. Note that when formation of sharp cutting blades at this time through pressing is possible, it is not necessary to grind all three surfaces of the triangular prism-shaped part 100a. A sharpened part 100d may be formed by grinding using a grindstone only the surface to be the inner or outer surface after it has been bent and then bent.

With the conventional triangular suture needle, the corners of the cross-sectional shape of the triangular prism-shaped part were rounded as with the rounded triangular prism-shaped part 100b of FIG. 3 when press forming the triangular prism-shaped part. As a result, the amount of grinding on the needle base side for forming sharp cutting blades at the corners increases, resulting in variances in the finished goods. On the contrary, according to the present invention, since the triangular prism-shaped part 100a on the needlepoint side is angular, the cutting blades are completed with little grinding, reducing variance, and thereby allowing a longer sharpened part 100d to form the cutting blades. Furthermore, since the mold for manufacturing the triangular suture needle of the present invention may be manufactured through simple processing, manufacturing costs may be kept low.

Note that the triangular suture needle of the present invention may be fabricated by forming a rounded triangular prism-shaped part corresponding to the entire pressed portion using a conventional press mold and then re-pressing and grinding only the needlepoint to complete the formation process; however, manufacturing costs increase due to pressing twice. On the contrary, when using the press mold of this embodiment, an angular triangular prism-shaped part and a rounded triangular prism-shaped part connecting to the needle base thereof may be formed through pressing only once, thereby keeping manufacturing costs low.

FIG. 5 is an oblique perspective of the triangular suture needle 100 according to the present invention. The triangular suture needle 100 shown in this diagram exemplifies an eyeless needle in which a hole 100h is formed in a base end 100g of the needle base using a laser; however, the present invention is not limited to the eyeless needle and is applicable to suture needles having a spring hole. In the case of the eyeless needle, a suture thread 20 is inserted through the hole 100h and crimped and fixed as described in the conventional example.

A sharp needlepoint 100e is formed at the tip of the triangular suture needle 100, and three cutting blades 100f continuing to the needlepoint 100e are formed. The sharpened part 100d attached to the cutting blades 100f is pointed (or tapered), gradually thicken up to the border with the nearly rounded triangular prism-shaped part 100b, and a step is formed at the rounded triangular prism-shaped part 100b. The cutting blades are formed along the entirety of the angular triangular prism-shaped part 100a, but the three cutting blades run almost parallel to each other on the needle base of the triangular prism-shaped part 100a, in other words, the tapering angle is nearly zero. Here, the tip end of the blade surfaces configuring the cutting blades of the sharpened part 100d may be removed by grinding to form the tip angle of the tip end of the sharpened part 100d equal to that of the sharpened part of the conventional triangular suture needle. Such configuration allows reduction in thrust resistance while maintaining resistance to bending at the tip.

When using this triangular suture needle 100 in surgical operations, it enters a living tissue from the needlepoint 100e and progresses while cutting open the living tissue with the cutting blades 100f. Until a region of the sharpened part 100d having a certain diameter increasing rate (tapering angle) or greater is passed, thrust resistance continues to increase, and begins to decrease before the entire sharpened part 100d is inserted. Once the sharpened part 100d is completely inserted, the rounded triangular prism-shaped part 100b then enters the living tissue. Therefore, since the region with a peak thrust resistance has cutting blades consistently, the suture needle is user friendly with little thrust resistance.

Furthermore, in the case of suturing a tough and thick living tissue, width of the thickest portion of the sharpened part 100d formed along the angular triangular prism-shaped part 100a is preferably greater than that of the rounded triangular prism-shaped part 100b. Since the rounded triangular prism-shaped part 100b has a small diameter, it can pass through the hole in the living tissue cut open by the sharpened part 100d without any further cutting. Therefore, the thrust resistance is negligible when the rounded triangular prism-shaped part 100b passes through the living tissue.

Figure 7A:
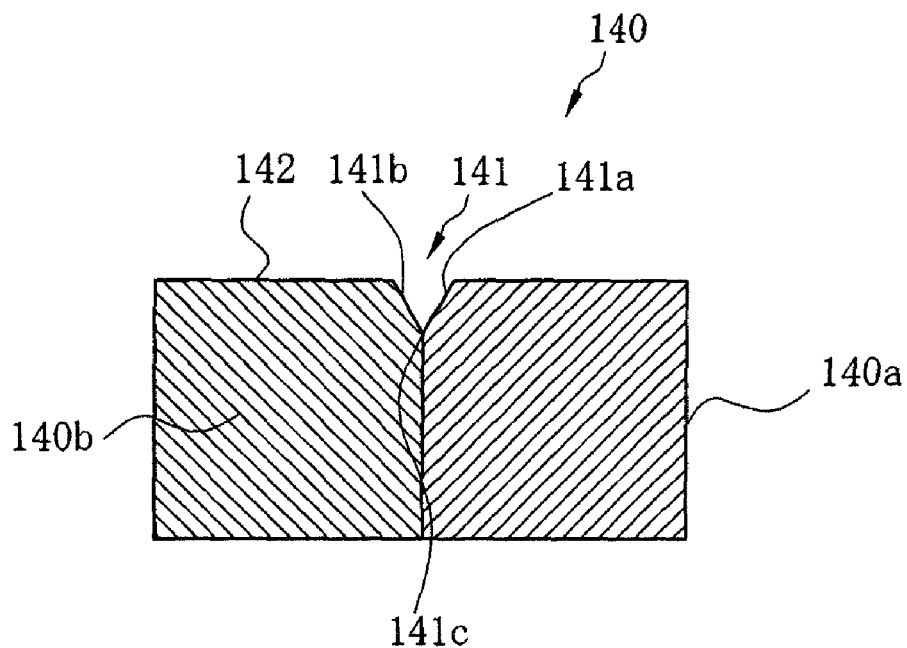
FIG. 7(a) is a cross section cut along the line F-F of FIG. 6.
Figure 7B:
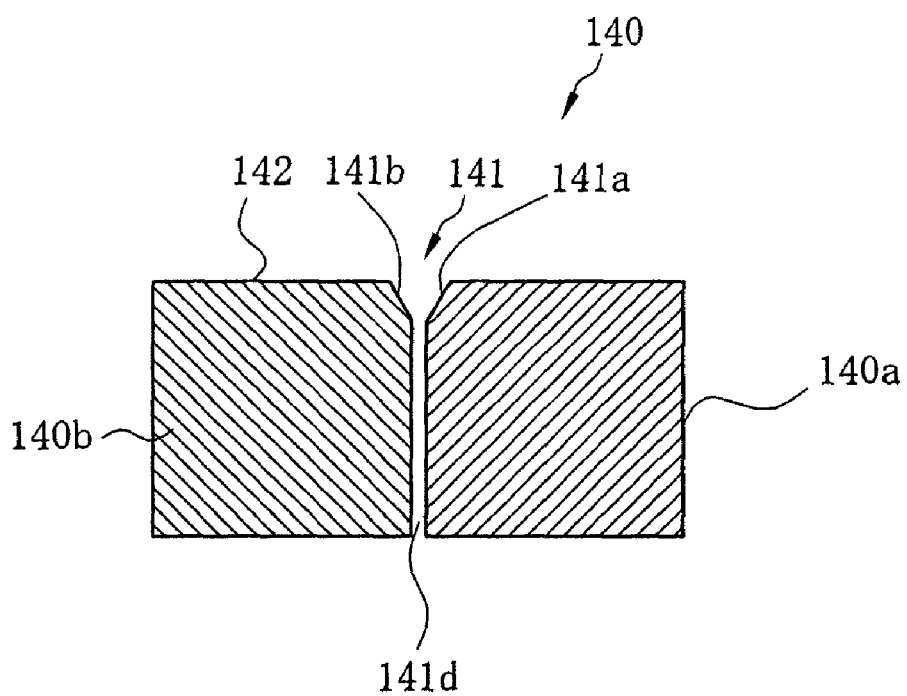
FIG. 7(b) is a cross section cut along the line G-G of FIG. 6.
Figure 9:
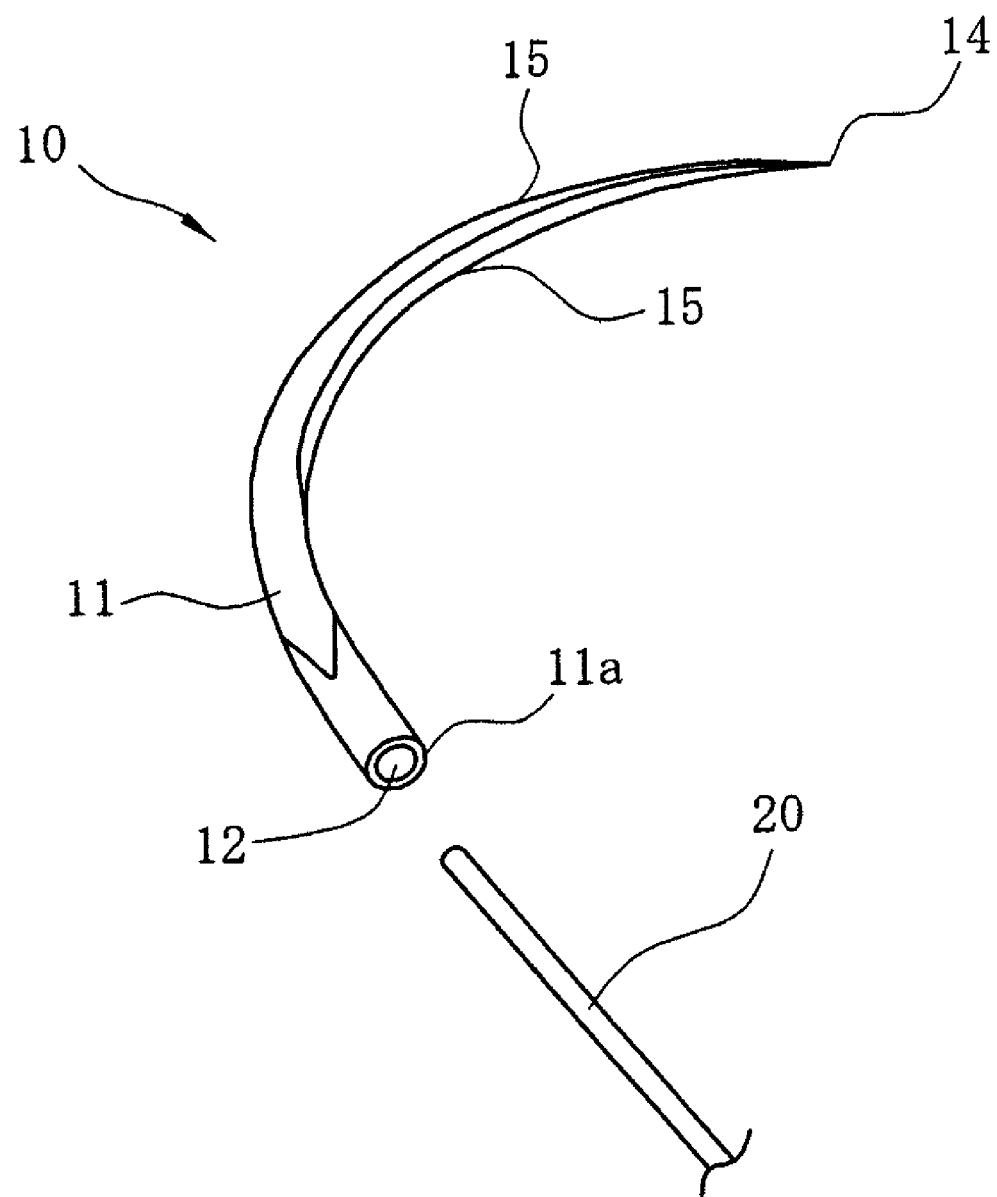
FIG. 9 is an oblique perspective of an exemplary conventional triangular suture needle.

FIGS. 6 and 7 show a press mold according to a second embodiment. With this mold, the undersurface 131 of an upper mold 130 is a flat surface. On the other hand, a lower mold 140 is divided into two lower molds 140a and 140b by a ridge line 141c between two surfaces 141a and 141b configuring a V-shaped groove 141. As shown in FIG. 7, the lower molds 140a and 140b are closely attached to each other on the needlepoint side for forming the angular triangular prism-shaped part 100a, and the lower molds 140a and 140b are separated from each other on the needle base side between which a gap 141d is formed, so as to form the rounded triangular prism-shaped part 100b. The top surface 142 of the lower mold 140 is in the same plane as those of the lower molds 140a and 140b. On the other hand, the upper mold press is different from the first embodiment and is constituted such that the angular triangular prism-shaped part and the rounded triangular prism-shaped part 100b can be pressed in the same plane.

While the cross section of the angular triangular prism-shaped part 100a of the suture needle formed using the press mold according to the second embodiment is an equilateral triangle, the rounded triangular prism-shaped part 100b has a slightly elongated shape protruding into the gap 141d, and the surfaces formed by the surfaces 141a and 141b of the V-shaped groove 141 have a slightly inward concave shape. In this manner, even the triangular prism-shaped part having the slightly concave surfaces is included in the rounded triangular prism-shaped part 100b of the present invention.

Note that when a bending strength test for the suture needle formed using the press mold according to the second embodiment was conducted (when the suture needle was bent 90 degrees towards the corner corresponding to the groove of the press mold) and compared to the conventional triangular suture needle, approximately 5% higher bending strength than the conventional triangular suture needle was found.

FIG. 8 is a chart showing results of a blind test for doctors to evaluate cutting ability of the conventional triangular suture needle and the triangular suture needle of the present invention. The suture needle formed using the mold according to the first embodiment is denoted as First Embodiment, and the suture needle formed using the mold according to the second embodiment is denoted as Second Embodiment, which are compared to a conventional triangular suture needle φ0.5. Cutting ability was evaluated by A (good), B (average), and C (poor), where 9 out of 10 doctors judged the suture needle of the present invention as good (A). On the other hand, 8 of 10 doctors evaluated the conventional needle as average, and there was one good and one bad evaluation as well. Reasons why evaluations of the suture needle of the present invention were good, as described above, may be conceived as the sharpened part 100d is elongated with a small tip angle, and cutting blades are consistently formed in the region with peak thrust resistance.

Note that by coating the cutting blades 100f with silicone, thrust resistance may further reduce. Furthermore, with this embodiment, while the rounded triangular prism-shaped part 100b on the needle base side connects to the thread attaching part 100c, they need not be connected and may be separated. Shape of the portion between the rounded triangular prism-shaped part 100b and the thread attaching part 100c when they are separated is arbitrary.

The invention claimed is:

1. A triangular suture needle, comprising: an angular triangular prism-shaped part on the needlepoint side; a rounded triangular prism-shaped part connecting to the needle base side of said triangular prism-shaped part; and a thread attaching part in a needle base end, wherein the angular triangular prism-shaped part is ground, forming a pointed, sharpened part with a sharp tip, and wherein the width of the thickest portion of the sharpened part is greater than width of the rounded triangular prism-shaped part.

* * * * *